(12) United States Patent
Wang et al.

(10) Patent No.: US 7,892,771 B2
(45) Date of Patent: Feb. 22, 2011

(54) CRYSTAL STRUCTURE OF SOLUBLE GLUTAMINYL CYCLASE

(75) Inventors: Andrew H.-J. Wang, Taipei (TW); Kai-Fa Huang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 12/429,721

(22) Filed: Apr. 24, 2009

(65) Prior Publication Data

US 2009/0203045 A1    Aug. 13, 2009

Related U.S. Application Data

(62) Division of application No. 11/362,051, filed on Feb. 24, 2006, now Pat. No. 7,572,614.

(51) Int. Cl.
| | |
|---|---|
| *C12N 9/00* | (2006.01) |
| *C12N 9/10* | (2006.01) |
| *C12N 9/86* | (2006.01) |
| *C12P 21/06* | (2006.01) |
| *G01N 31/00* | (2006.01) |
| *G06F 19/00* | (2006.01) |
| *G06G 7/48* | (2006.01) |

(52) U.S. Cl. ............ 435/7.71; 435/193; 435/231; 435/69.1; 435/183; 702/11; 702/27

(58) Field of Classification Search ............ None
See application file for complete search history.

(56) References Cited

U.S. PATENT DOCUMENTS

| 6,117,663 A | 9/2000 | Boriack-Sjodin et al. |
|---|---|---|
| 2004/0224875 A1 | 11/2004 | Schilling et al. |
| 2005/0181975 A1 | 8/2005 | Griffith et al. |
| 2005/0202550 A1 | 9/2005 | Pandit |

FOREIGN PATENT DOCUMENTS

| WO | 2004098591 A2 | 11/2004 |
|---|---|---|
| WO | 2004098625 A2 | 11/2004 |

OTHER PUBLICATIONS

Azarkan et al., Crystallization and preliminary X-ray diffraction studies of the glutaminyl cyclase from Carica papaya latex, Acta Cryst., published online on 23, Oct. 2004, F61, p. 59-61 .
Booth, et al., "Human glutaminyl cyclasse and bacterial zinc aminopeptidase share a common fold and active site", BMC Biology, vol. 2, No. 2 (2004).
Branden et al., "Introduction to Protein Structure Second Edition", Garland Publishing Inc., New York, 1999.
Bubsy, et al., "An enzyme(s) that converts glutaminyl-peptides into pyroglutamyl-peptides", The Journal of Biological Chemistry, vol. 262, No. 18, pp. 8532-8536 (1987).
Drenth, "Principles of X-ray Crystallography," Springer, New York, 1995.
Ezura, et al., "Association of multiple nucleotide variations in the pituitary glutaminyl cyclase gene (QPCT) with low radial BMD in adult women", Journal of Bone and Mineral Research, vol. 19, pp. 1296-1301 (2004).
Fischer, et al., "Identification of a mammalian glutaminyl cyclase converting glutaminyl into pyroglutamyl peptides", Proceedings of the national academy of sciences of the United States of America, No. 84, pp. 3628-3632 (1987).
Harigaya, et al., "Amyloid beta-protein starting pyroglutamate at position 3 is a major component of the amyloid deposits in the alzheimer's disease brain", Biochemical and Biophysical Research Communications, vol. 276, pp. 422-427 (2000).
Hinke, et al. "Dipeptidyl Peptidase IV (DPIC/DC26) Degradation of Glucagon", Journal of Biological Chemistry, vol. 275, pp. 3827-3834 (2000).
Huang, et al., "Cloning, expression, characterization, and crystallization of a glutaminyl cyclasse from human bone marrow: A single zinc metalloenzyme", Protein Expression & Purification, vol. 43, pp. 65-72 (2005).
Huang, et al., "Crystal structures of human glutaminyl cyclase, an enzyme responsible for protein N-terminal pyroglutamate formation", PNAS, vol. 102, No. 37, pp. 13117-13122 (2005).
Keirzek et al., Biophys Chem 91:1-20, 2001.
Kuo, et al., "Isolation, chemical characterization, and quantitation of a beta 3-pyroglytamyl peptide from neuritic plaques and vascular amyloid deposits", Biochemical and Biophysical Resarch Communications, vol. 237, pp. 188-191 (1997).
Morgan, et al., "Structure and function of amyloid in Alzheimer's disease", Progress in Neurobiology, vol. 74, pp. 323-349 (2004).
Ngo et al., in The Protein Folding problem and Tertiary Structure Prediction, 1994, Merz et al. (ed.), Birkhauser, Boston, MA, pp. 433 and 492-495.
Oberg, et al., "Papaya glutamine cyclase, a plant enzyme highly resistant to proteolysis, adopts an all-b conformation", European Journal of Biochemistry, vol. 258, pp. 214-222 (1998).
Pawlak, Joanna et al., "Snake vermon glutaminyl cyclase," Toxicon, 48:278-286 (2006).
Russo, et al., "Pyroglutamate-modified amyloid beta-peptides strongly affect cultured neuron and astrocyte survival", Journal of Neurochemistry, vol. 82, pp. 1480-1489 (2002).

(Continued)

*Primary Examiner*—Suzanne M Noakes
*Assistant Examiner*—Jae W Lee
(74) *Attorney, Agent, or Firm*—Panitch Schwarze Belisario & Nadel LLP (57) ABSTRACT

A crystalline structure of glutaminyl cyclase (QC) is described. Also described are the methods of preparing the crystalline structure of QC and the methods for identifying candidate inhibitors of QC. In addition, a structural basis for the rational design or identification of new inhibitors that may be used to treat QC-associated disorders is also described.

10 Claims, 7 Drawing Sheets

(7 of 7 Drawing Sheet(s) Filed in Color)

OTHER PUBLICATIONS

Saido, et al., "Dominant and differential deposition of distinct beta-amyloid peptide species, A beta N3(pE), in senile plaques", Neuron, vol. 14, pp. 457-466 (1995).

Schilling, et al., "Heterologous expression and characterization of human glutaminyl cyclase: evidence for a disulfide bond with importance for catalytic activity", Biochemistry, vol. 41, pp. 10849-10857 (2002).

Schilling, et al., "Glutaminyl cyclases unfold glutaminyl cyclases activity under mild acid conditions", FEBS Letters, vol. 563, pp. 191-196 (2004).

Schilling, Stephan et al., "Substrate specificity of glutaminyl cyclases from plants and animals," Biol. Chem., 384:1583-1592 (Dec. 2003).

Shilling, et al., "Identification of human glutaminyl cyclase as a metalloenzyme", Journal of Biological Chemistry, vol. 278, pp. 29773-29779 (2003).

Stewart, et al., "Role of genetic factors in the pathogenesis of osteoporosis", Journal of Endocrinology, vol. 166, p. 235-245 (2000).

Sykes, et al., "Evidence for tissue-specific forms of glutaminyl cyclase", FEBS Letters, vol. 455, pp. 159-161 (1999).

Van Coillie, et al., "Functional comparison of two human monocyte chemotactic protein-e isoforms, role of the amino-terminal pyroglutamic acid and processing by CD26/Dipeptidyl Peptidase IV", Biochemistry, vol. 37, pp. 12672-12680 (1998).

Wintjens, Rene et al., "Crystal structure of papaya glutaminyl cyclase, an archetype for plant and bacterial glutaminyl cyclases," J. Mol. Biol., 357: 457-470 (2006).

Wishart et al., Journal of Biological Chemistry, vol. 270, No. 45, pp. 26782-26785, 1995.

Witkowski et al., Biochemistry, 38, 11643-11650, 1999.

Zerhouni, Samira et al., "Purification and characterization of papaya glutamine cyclotransferase, a plant enzyme highly resistant to chemical, acid and thermal denaturation," Biochimica et Biophysica Acta, 1387:275-290 (1998).

Dirr, Heini et al., "X-ray crystal structures of cytosolic glutathione S-transferases Implications for protein architecture, substrate recognition and catalytic function," Eur. J. Biochem. 220, 645-661 (1994).

Sun, Lei et al., "Crystal structure of the pyridoxal-5'-phosphate-dependent serine dehydratase from human liver," Protein Science, 2005 14:791-798.

Yamada, Taro et al., "Crystal Structure of Serine Dehydratase from Rat Liver," Biochemistry 2003, 42, 12854-12865.

CRYSTAL STRUCTURE OF SOLUBLE GLUTAMINYL CYCLASE

REFERENCE TO RELATED APPLICATIONS

This application is a divisional patent application of U.S. patent application Ser. No. 11/362,051, filed on Feb. 24, 2006, titled "Crystal Structure Of Soluble Glutaminyl Cyclase," published Aug. 30, 2007, as U.S. patent publication No. 20070202586 A1, issued as U.S. Pat. No. 7,572,614 on Aug. 11, 2009, which is hereby incorporated by reference herein in its entirety.

BACKGROUND OF THE INVENTION

The present invention relates to a crystal structure, and more particularly to the crystal structure of glutaminyl cyclase (QC).

The formation of N-terminal pGlu is an important post-translational or co-translational event in the processing of numerous bioactive neuropeptides, hormones, and cytokines during their maturation in the secretory pathway. The N-terminal pGlu is necessary in the formation of the proper conformation of these regulatory peptides for binding to their receptors and/or for protecting the N-termini of these peptides from exopeptidase degradation (Van Coillie et al., *Biochemistry* 37: 12672-12680 (1998); Hinke et al., *J. Biol. Chem.* 275: 3827-3834 (2000)). The N-terminal pyroglutamate (pGlu) is formed by the N-terminal cyclization of its glutaminyl precursor. And the glutaminyl cyclases (QCs) are the catalysts responsible for this posttranslational modification (Fischer et al., *Proc. Natl. Acad. Sci. USA* 84: 3628-3632 (1987); Busby et al., *J. Biol. Chem.* 262: 8532-8536 (1987)).

QCs (EC 2.3.2.5) are acyltransferases identified in both animal and plant sources (Fischer et al., *Proc. Natl. Acad. Sci. USA* 84: 3628-3632 (1987); Busby et al., *J. Biol. Chem.* 262: 8532-8536 (1987); Oberg et al., *Eur. J. Biochem.* 258: 214-222 (1998)). QCs are abundant in mammalian neuroendocrine tissues, such as hypothalamus and pituitary (Busby et al., *J. Biol. Chem.* 262: 8532-8536 (1987); Sykes et al., *FEBS Lett.* 455: 159-161 (1999)), and are highly conserved from yeast to human. Animal QCs were shown to have distinct structure and protein stability from plant QCs in spite of their similar molecular masses, i.e., 33-40 kDa (Oberg et al., *Eur. J. Biochem.* 258: 214-222 (1998); Schilling et al., *Biochemistry* 41: 10849-10857 (2002)). While no bacterial QCs have been reported thus far, the mammalian QCs had been predicted to exhibit remarkable homology to the bacterial double-zinc aminopeptidases (Schilling et al., *J. Biol. chem.* 278: 49773-49779 (2003); Booth et al., *BMC biol.* 2: 2 (2004)).

Several of human genetic diseases, e.g., osteoporosis that is a multifactorial hormonal disease characterized by reduced bone mass and microarchitectual deterioration of bone tissue (Stewart et al., *J. Endocrinol.* 166: 235-245 (2000)), appear to result from mutations of the QC gene. The gene encoding QC (QPCT) lies on chromosome 2p22.3. Within the region, thirteen single nucleotide polymorphisms (SNPs) were analyzed and shown a striking correlation with osteoporosis susceptibility in adult women (Ezura et al., *J Bone Miner. Res.* 19: 1296-1301 (2004)). Of these SNPs, the R54W presents, statistically, the most prominent association with osteoporosis, which was proposed to affect the pathogenesis through the hypothalamus-pituitary-gonadal axis (Ezura et al., *J. Bone Miner. Res.* 19: 1296-1301 (2004)).

Interestingly, QC also catalyzes the N-terminal glutamate cyclization that leads to the formation pGlu (Schilling et al., *FEBS Lett.* 563: 191-196 (2004)). This reaction is probably related to the formation of several plaque-forming peptides, such as amyloid-β (Aβ) peptides and CLAC (collagen-like Alzheimer amyloid plaque component), which play a pivotal role in Alzheimer's disease (Morgan et al., *Prog. Neurobiol.* 74: 323-349 (2004); Hashimoto et al., *EMBO J.* 21: 1524-1534 (2002)). Peptides containing N-terminal pGlu, e.g., pGlu$^3$-Aβ peptides, are major fractions of the Aβ peptides within the core of neuritic plaques (Saido et al., *Neuron* 14: 457-466 (1995); Kuo et al., *Biochem. Biophys. Res. Commun.* 237: 188-191 (1997); Russo et al., *J. Neurochem.* 82: 1480-1489 (2002)). The N-terminal pGlu could enhance the hydrophobicity, proteolytic stability and neurotoxicity of these peptides (Russo et al., *J. Neurochem.* 82: 1480-1489 (2002); Harigaya et al., *Biochem. Biophys. Res. Commun.* 276: 422-427 (2000)), probably causing a profused accumulation of pGlu-Aβ peptides in several senile plaques, and thus accelerating the progression of neurodegenerative disorders.

To date, there remains several theories concerning the properties and structures of human and animal QCs. The present invention offers the crystal structure of QC in free form, the structures of the active sites or catalytic centers of the QC, the method for identifying an inhibitor of glutaminyl cyclase (QC), and provides a structural basis for the rational design of new inhibitors against QC-associated disorders.

BRIEF SUMMARY OF THE INVENTION

An aspect of the invention provides a crystalline structure of glutaminyl cyclase (QC).

In another example, the present invention provides crystalline compositions of a complex comprising at least one QC molecule and another molecule that ligates, interacts with, or otherwise binds to the QC molecule.

Another aspect of the invention provides a method for identifying an inhibitor of glutaminyl cyclase (QC). The method comprises the steps of: (a) preparing QC protein, preferably a polypeptide with an amino acid sequence from amino acid residues 33 to 361 of SEQ ID NO:1, wherein the polypeptide has an active site comprising one zinc ion tetrahedrally coordinated to amino acid residues 159, 202, and 330 of SEQ ID NO:1, and a water molecule; (b) contacting the polypeptide with a candidate inhibitor for forming a QC/inhibitor complex; (c) generating a three-dimensional model of the QC/candidate inhibitor complex obtained in step (b); wherein the candidate inhibitor having an imidazole nitrogen bound to the zinc ion is identified as the inhibitor of QC.

A further aspect of the invention provides a method of making a QC crystal. The method comprises the steps of: (a) expressing a QC protein; (b) purifying the QC protein; and (c) crystallizing the QC protein to form the QC crystal.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

To facilitate the understanding of the invention, a number of terms are defined below.

The term "active site" refers to a specific region (or atom) in a molecular entity that is capable of entering into a stabilizing interaction with another molecular entity. In certain embodiments, the term also refers to the reactive parts of a macromolecule that directly participate in its specific combination with another molecule. In other embodiments, a binding site may be comprised or defined by the three dimensional arrangement of one or more amino acid residues within a folded polypeptide.

The term "analogue" refers to a drug or chemical compound whose structure is related in some way to that of another drug or chemical compound, but whose chemical and biological properties may be similar or different.

The term "coordinate" or "structural coordinates" refers to Cartesian coordinates derived from the mathematical equations related to the patterns obtained on diffraction of a monochromatic beam of X-ray by the atoms of a protein or protein complex in crystal form. The diffraction data are used to calculate an electron density map of the repeating units of the crystal. The electron density maps are then used to establish the positions of the individual atoms of the molecule or molecular complex.

Figure 1:
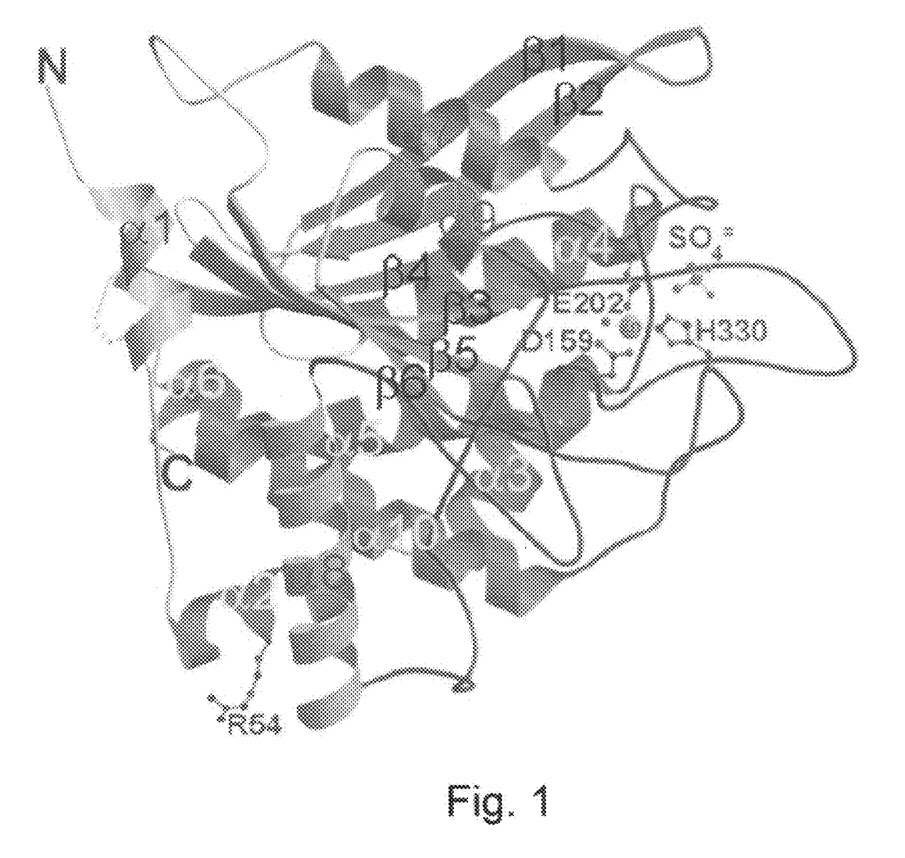
FIG. 1 is an overall view of the structure of human QC.

The term "atomic structure coordinates of the human glutaminyl cyclase crystal at pH 6.5" refers to the atomic structure coordinates provided in FIG. 1 of U.S. patent application Ser. No. 11/362,051, filed on Feb. 24, 2006, which is hereby incorporated by reference in its entirety.

Figure 2:
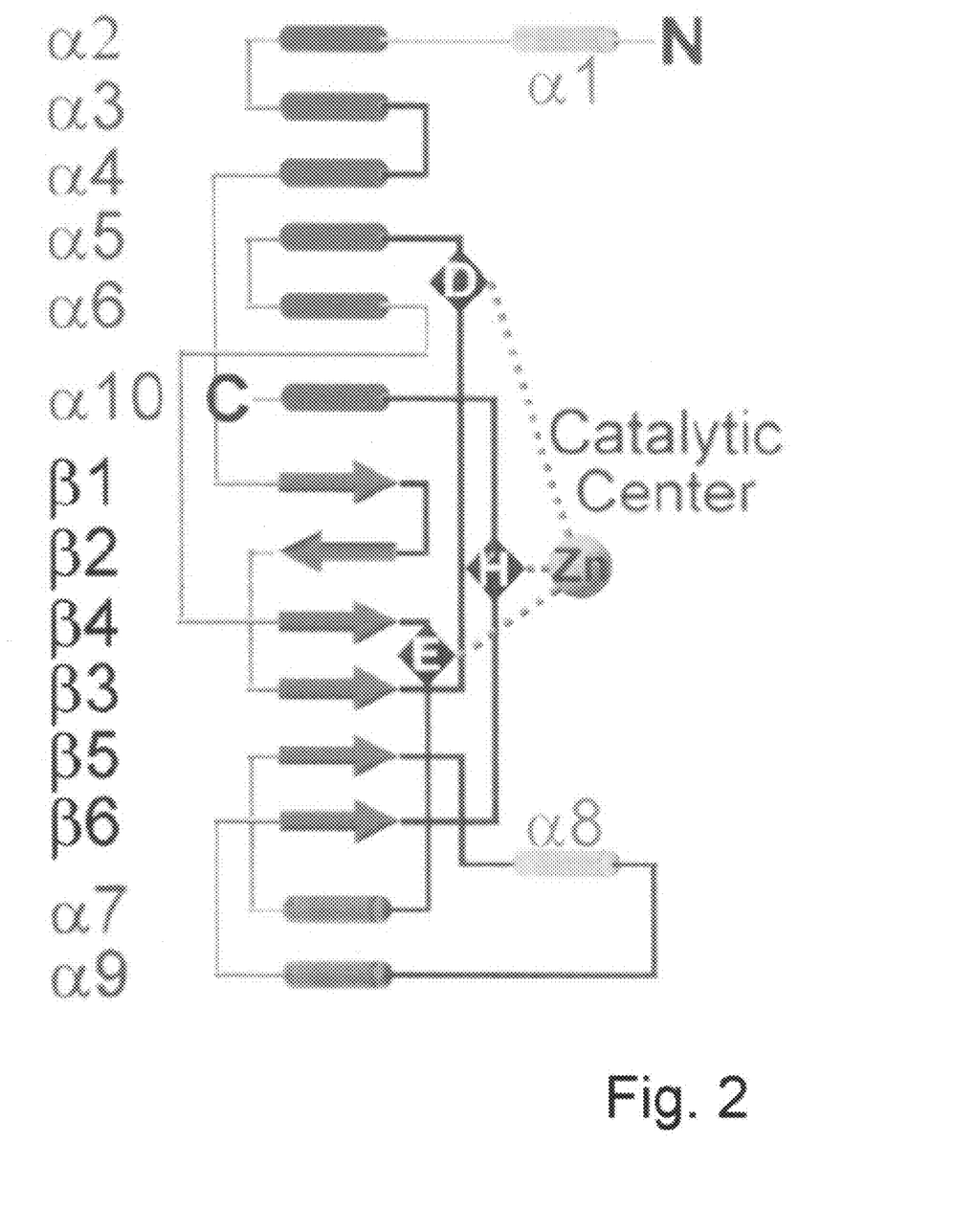
FIG. 2 is a schematic diagram illustrating a topology of the human QC structure.

The term "atomic structure coordinates of the human glutaminyl cyclase crystal at pH 8.0" refers to the atomic structure coordinates provided in FIG. 2 of U.S. patent application Ser. No. 11/362,051, filed on Feb. 24, 2006, which is hereby incorporated by reference in its entirety.

Figure 4:
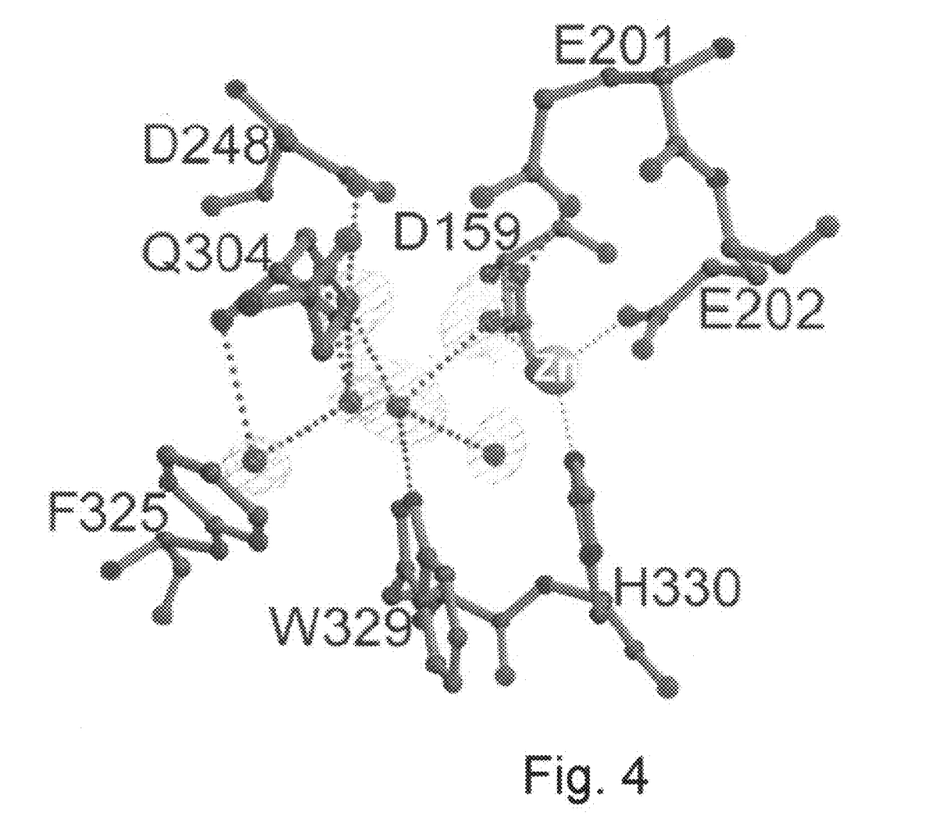
FIG. 4 depicts the active-site structure of a human QC in free form.

The term "atomic structure coordinates of the crystal of the human glutaminyl cyclase in complex with glutamine t-butyl ester" refers to the atomic structure coordinates provided in FIG. 4 of U.S. patent application Ser. No. 11/362,051, filed on Feb. 24, 2006, which is hereby incorporated by reference herein in its entirety.

The term "homologue" means a protein, polypeptide, oligopeptide, or portion thereof, having an amino acid sequence identity with QC as described in SEQ ID No: 1, or any active site described herein, or any functional or structural domain of binding protein. SEQ ID No:1 is a partial amino acid sequence of human QC.

The term "substrate" refers to any molecule, which is acted upon by an enzyme. According to the invention, the substrate binds with an active site of QC to form a QC-substrate-complex.

The term "mature domain" refers to a portion or segment of the QC protein or homologue that comprises an active or catalytic site; that is, the polypeptide with an amino acid sequence of amino acid residues 33 to 361 of SEQ ID NO:1.

The term "root mean square deviation" refers to the square root of the arithmetic mean of the squares of the deviations from the mean. It is a way to express the deviation or variation from a trend or object.

The term "variants" in relation to the polypeptide sequence in SEQ ID NO:1 include any substitution of, variation of, modification of, replacement of, deletion of, or addition of one or more amino acids from or to the sequence providing a resultant polypeptide sequence for a protein having QC activity.

The following amino acid abbreviations are used throughout this disclosure:

A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanin; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; H=His=Histidine.

A. Cloning, Expression and Purification

The nucleotide sequence encoding QC, or functional fragment, derivatives thereof, can be inserted into an appropriate expression vector that contains the necessary elements for the transcription and translation of the inserted protein-coding sequence. The vectors are then introduced into the desired host cells by methods known in the art.

For detailed descriptions of ways for cloning, expression, and purification of QC, please refer to U.S. patent application Ser. No. 11/331,704, the disclosure of which is hereby incorporated herein by reference.

B. Crystal Structure

X-ray structure coordinates define a unique configuration of points in space. Those skilled in the art understand that a set of structure coordinates for a protein or an enzyme/substrate complex define a set of points that, in turn, define a configuration in three dimensions. A similar or identical configuration can be defined by an entirely different set of coordinates, provided the distances and angles between atomic coordinates remain essentially the same.

Three-dimensional data generation may be provided by an instruction or set of instructions, such as a computer program or commands for generating a three-dimensional structure or graphical representation from structure. The graphical representation can be generated or displayed by commercially available software programs, such as SOLVE, RESOLVE (Terwilliger et al., *Methods Enzymol.* 374: 22-37 (2003)), O (Jones et. al., Acta Crystallogr. A47: 110-119 (1991)), PROCHECK (Laskowski et al., *J. Appl. Crystallogr.* 26: 283-291 (1993)), MOLSCRIPT (Kraulis et al., *J appl. crystallogr.* 24: 946-950 (1991)), Raster3D (Merrit & Bacon et al., *Methods Enzymol.* 277: 505-524 (1997)) and GRASP (Nicholls et al., *Proteins* 11: 281-296 (1991)), which are incorporated herein by reference.

The present invention provides a crystalline structure of a QC polypeptide, the polypeptide comprising a QC protein, preferably a polypeptide an amino acid sequence spanning amino acid residues 33 to 361 of SEQ ID NO: 1. One embodiment of the present invention provides crystalline composition of QC that is derived from a mammal. In another embodiment, the present invention provides a crystal structure of QC that is derived from a human being.

The present invention further provides a crystal structure of human QC that comprises a three-dimensional structure characterized by the atomic structure coordinates of the human QC crystal at pH 6.5. And in accordance with another embodiment, the present invention provides a crystal structure of human QC, that has a space group of H32 so as to form unit cell dimensions of a=b=119.03 Å, c=332.94 Å. In yet another embodiment, the present invention provides a crystal as characterized above, wherein the crystal diffracts x-rays for determination of atomic coordinates of the crystal to a resolution of about 1.66 Å.

The present invention further provides a crystal structure of human QC that comprises a three-dimensional structure characterized by the atomic structure coordinates of the human QC crystal at pH 8.0. In another embodiment, the present invention provides a crystal structure of human QC, that has a space group of H32 so as to form unit cell dimensions of a=b=118.99 Å, c=332.26 Å. In yet another embodiment, the present invention provides a crystal as characterized above, wherein the crystal diffracts x-ray for determination of atomic coordinates of the crystal to a resolution of about 2.35 Å.

In one embodiment, the present invention provides a QC crystal comprising two QC molecules. In accordance with another embodiment, the invention provides the crystal as characterized above, wherein the two QC molecules have a root mean square deviation of about 0.386 Å for all $C^\alpha$ atoms between the two QC molecules.

The mature domain (amino acid residues 33-361 of SEQ ID NO: 1) of human QC was shown to possess glutaminyl and glutamyl cyclase activities on the putative physiological substrate of human QC. The asymmetric unit of the crystals, grown at pH 6.5, contains two human QC molecules with a root mean square deviation of 0.386 Å (for all $C^\alpha$ atoms) between them. The globular structure reveals a mixed $\alpha/\beta$ fold with a size of 63×58×41 Å$^3$. There are up to 36% and 16% of the amino acid residues involved in $\alpha$-helix and $\beta$-sheet, respectively, with 6% in the $3_{10}$-helix regions.

FIG. 1 is an overall view of the structure of human QC. The central six $\beta$-strands are colored orange. The $\alpha$ helices located on the top, bottom, and edge are colored cyan, magenta, and yellow, respectively. The zinc ion is shown as a yellow sphere. The zinc-coordinated residues, Arg54, and a sulfate ion are depicted with a ball-and-stick model. The coils and loops adjacent to the catalytic center are colored green, whereas those distant from the active site are colored gray. Gray dots further represent the disordered region of residues 183 to 188 of SEQ ID NO: 1. FIG. 2 is a schematic diagram illustrating a topology of the human QC structure. The color codes for secondary structural elements are identical to those in FIG. 1.

Referring to both FIGS. 1 and 2, the structure has an open-sandwich topology comprising a central six-stranded $\beta$-sheet surrounded by two $\alpha$-helices ($\alpha$7 and $\alpha$9) and six additional ($\alpha$2, $\alpha$3, $\alpha$4, $\alpha$5, $\alpha$6 and $\alpha$10) $\alpha$-helices on opposite sides, and flanked by two other $\alpha$-helices ($\alpha$1 and $\alpha$8) at one edge of the $\beta$-sheet (FIG. 1). This twisted $\beta$-sheet is formed by two anti-parallel strands ($\beta$1 and $\beta$2) and four parallel strands ($\beta$3, $\beta$4, $\beta$5 and $\beta$6), constituting the hydrophobic core of the molecule. The coil and loop regions of the structure represent 42% of the total residues; about half of them are major components of the active site (FIG. 2). The structures at pH 6.5 and pH 8.0 are essentially similar, and the structure at pH 8.0 has a root mean square deviation of 0.155 Å (for all $C^\alpha$ atoms) between the QC molecules.

C. QC/QC Substrate Complex

In another aspect, this invention provides a crystal of a complex comprising QC and a QC substrate bound to QC.

In one embodiment, the crystal of the QC/QC substrate complex comprises: (a) a polypeptide with an amino acid sequence from residues 33 to 361 of SEQ ID NO:1, or a homologue, analogue or variant thereof, and (b) a QC substrate, such that the crystal effectively diffracts X-rays for the determination of atomic coordinates of the QC/QC substrate complex to a resolution of 2.22 Å.

Another embodiment of this invention provides a QC/QC substrate complex that comprises a three-dimensional structure characterized by the atomic coordinates of the crystal of the human QC in complex with glutamine t-butyl ester.

In yet another embodiment, this invention provides a QC/QC substrate complex that has a space group of H32, so as to form a unit cell dimensions of a=b=119.14 Angstroms, and c=332.61 Angstroms.

Similarly, the three-dimensional data of the crystal of the QC/QC substrate complex may be generated by an instruction or set of instructions, such as a computer program or commands for generating a three-dimensional structure or graphical representation from structure. The graphical representation can be generated or displayed by commercially available software programs, such as those described in the method for determining the QC crystal structure.

D. Identification of Inhibitor of QC

To use the structure coordinates generated for QC, homologues, thereof, or one of its active site, it is at times necessary to convert them into a three-dimensional shape or to extract three-dimensional structural information from them. One of ordinary skill in the art would know that this can be achieved through the use of commercially or publicly available software that is capable of generating a three-dimensional structure, or a three-dimensional representation, of molecules or portions thereof from a set of structure coordinates.

The present invention provides a method for identifying an inhibitor of glutaminyl cyclase (QC), comprising the steps of:

(a) preparing a polypeptide with an amino acid sequence from amino acid residues 33 to 361 of SEQ ID NO:1, wherein the polypeptide has an active site comprising one zinc ion tetrahedrally coordinated to amino acid residues 159, 202, and 330 of SEQ ID NO:1, and a water molecule;

(b) contacting the polypeptide with a candidate inhibitor for forming a QC/candidate inhibitor complex;

(c) generating a three-dimensional model of the QC/candidate inhibitor complex obtained in step (b);

wherein the candidate inhibitor having an imidazole nitrogen bound to the zinc ion is identified as the inhibitor of QC.

The active site may further comprise amino acid residues 201, 207, 248, 305, 325, and 329 of SEQ ID NO: 1.

In accordance with one embodiment, the active site of QC comprises a water molecule, a zinc ion tetrahedrally coordinated to amino acid residues 159, 202, and 330 of SEQ ID NO: 1, and the amino acid residue 160 of SEQ ID NO: 1, the amino acid residue 160 of SEQ ID NO: 1 forming a peptide bond with the amino acid residue 159 of SEQ ID NO: 1. In another embodiment, such peptide bond is stabilized by a plurality of hydrogen bonds and is cis-configured.

In yet another embodiment, the active site of QC further comprises a hydrophobic pocket lined by amino acid residues 144, 146, 154, 249, 303, 321, 325, and 329 of SEQ ID NO: 1. Additionally, the active site may further comprise a sulfate ion adjacent to the hydrophobic pocket, wherein the sulfate ion is hydrogen-bonded to the amino acid residues 144, 206, 207, and 330 of SEQ ID NO: 1, and at least two water molecules.

Similarly, the three-dimensional data of the QC/candidate inhibitor complex may be generated by an instruction or set of instructions, such as a computer program or commands for generating a three-dimensional structure or graphical representation from structure. The graphical representation can be generated or displayed by commercially available software programs, such as those described above for determining the QC crystal structure and QC/QC substrate complex crystal structure.

Figure 5:
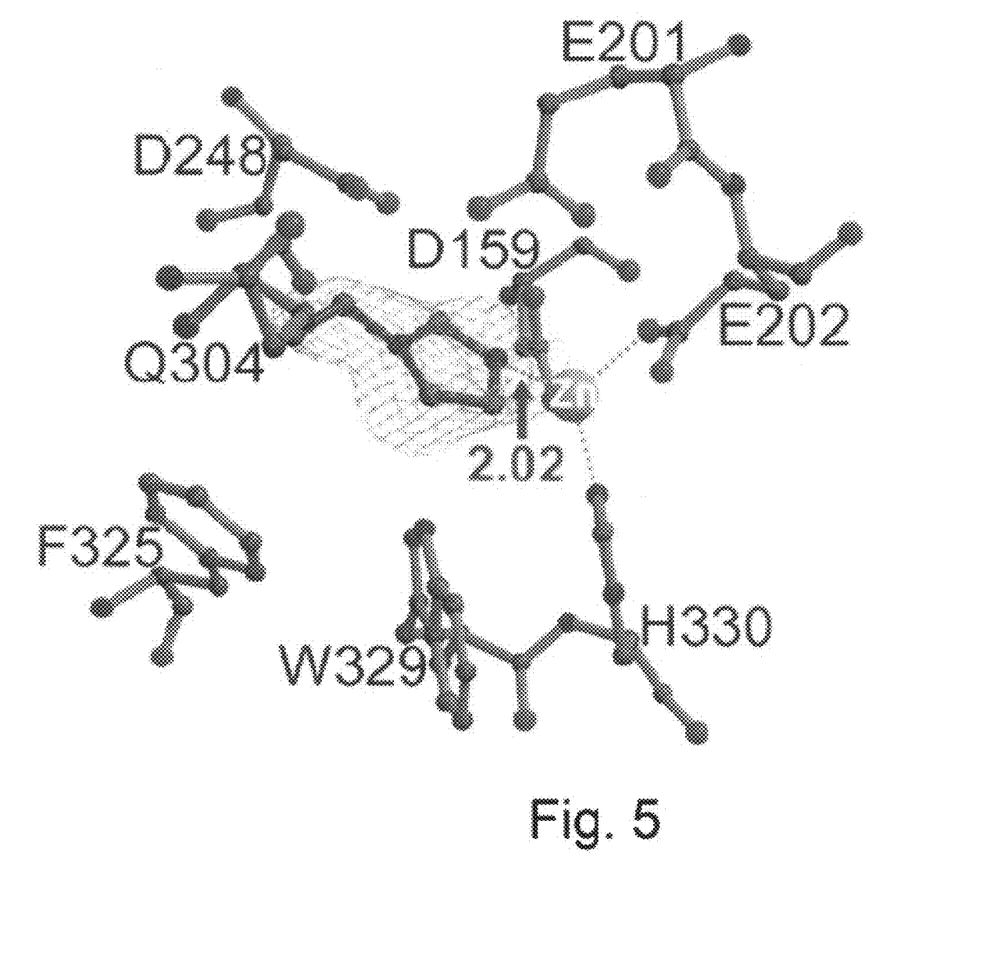
FIG. 5 depicts the active-site structure of a human QC bound to 1-vinylimidazole at a 1.68 Å resolution.
Figure 6:
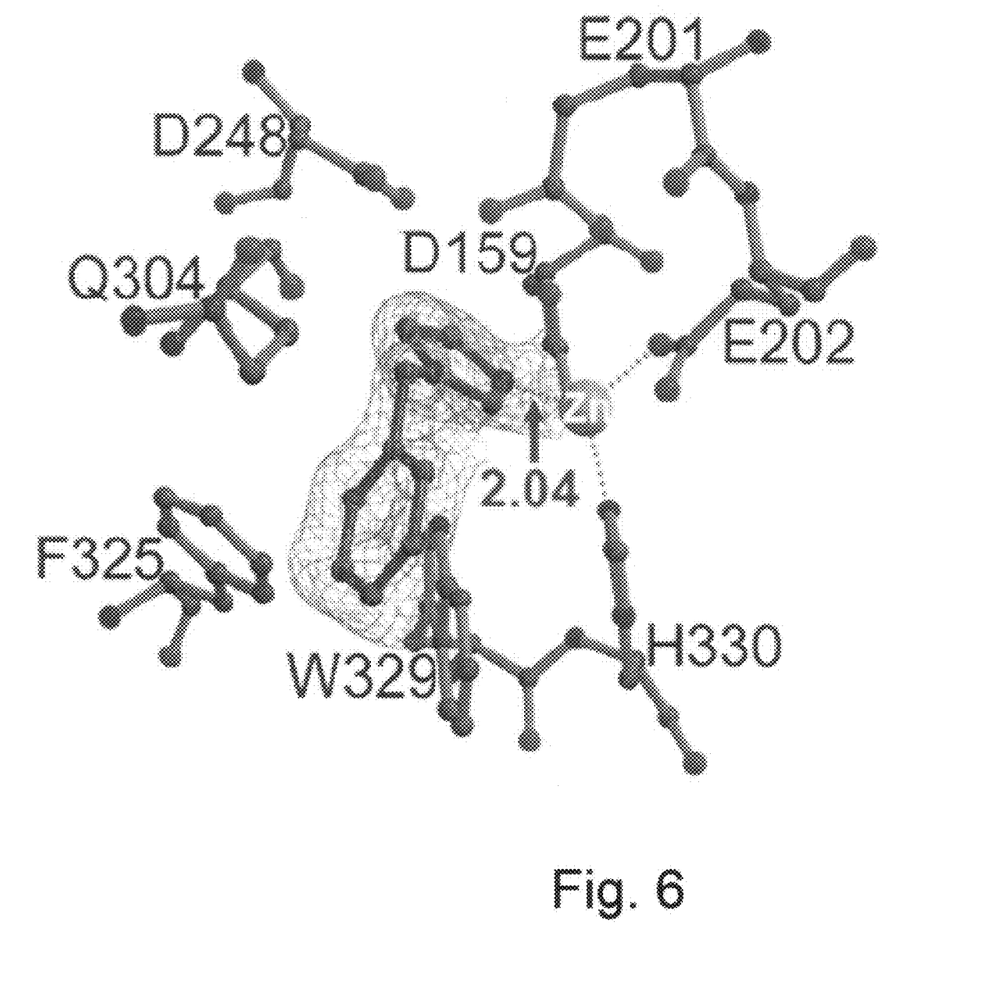
FIG. 6 depicts the active-site structure of a human QC bound to 1-benzylimidazole at a 1.64 Å resolution.
Figure 7:
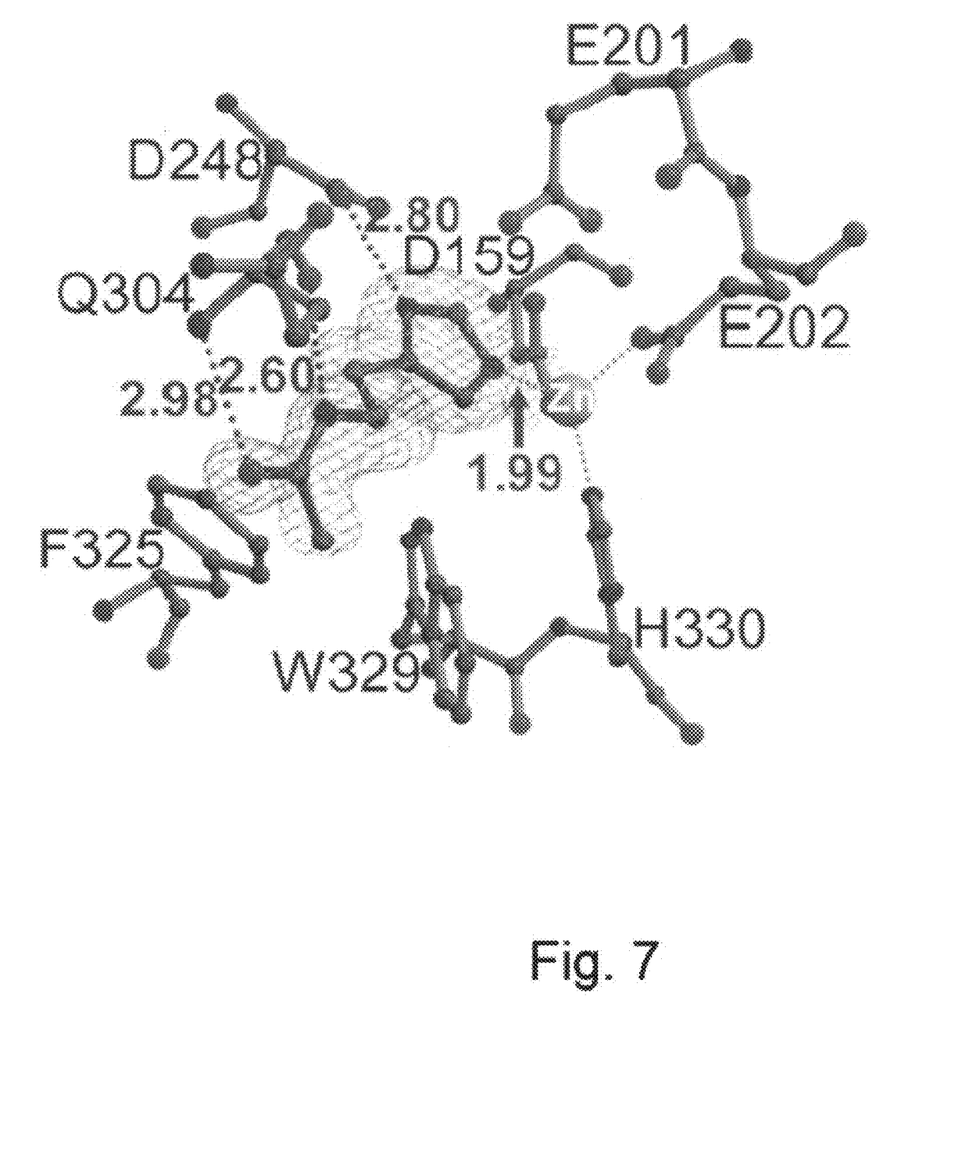
FIG. 7 depicts the active site structure of a human QC bound to N-ω-acetylhistamine at a 1.56 Å resolution.

The inhibitor includes but is not limited to imidazole-derived inhibitors, such as 1-vinylimidazole, 1-benzylimidazole, N-ω-acetylhistamine. For example, an electron-rich nucleophile having a good ability to ligate to the zinc ion of human QC, and combined with bulky hydrophobic substituents may also be the structural basis of a potent QC inhibitor. As shown in FIG. 5 through to 7, binding of the inhibitors results in the removal of six water molecules within the active-site pocket, including the zinc-coordinated one which is replaced by an imidazole nitrogen of the inhibitors.

The QC structure coordinates or the three-dimensional graphical representation generated from the coordinates may be used in conjunction with a computer for a variety of purposes, including identifying a inhibitor of QC. Various computational methods may also be used to determine whether a molecule or an active site thereof is "structurally equivalent" in terms of its three-dimensional structure to all or part of QC or its active site. One of ordinary skill in the art would understand that such methods may be carried out using software applications currently available.

E. Method of Making Crystal of Glutaminyl Cyclase

The present invention provides a method of making the crystal of human QC.

In one embodiment, the method of making the crystal of human QC comprises: (a) expressing the QC protein; (b) purifying the QC protein; and (c) crystallizing the QC protein to form the crystal of human QC. Preferably, the QC protein is crystallized by a hanging-drop vapor diffusion method.

F. Screening Drugs

Once a potential substrate is identified, it can be either selected from a library of chemicals as are commercially available from most large chemical companies. Alternatively, the potential substrate can be synthesized de novo.

When a suitable drug is identified, a supplemental crystal can be grown comprising a complex formed of the QC crystal and the drug. Preferably, the supplemental crystal effectively diffracts X-rays allowing the determination of the atomic coordinates of the QC/drug complex to a resolution of less than 3.0 Angstroms, and preferably less than 2.0 Angstroms.

The present invention contemplates methods for treating certain diseases in a mammal, preferably, human, by using the substrates, and preferably the inhibitors, as described herein.

The invention will now be described in further detail with reference to the following specific, non-limiting examples.

Example 1

Expression and Purification of Human QC

The cDNA encoding human QC was amplified by PCR from a human bone marrow cDNA library (Clontech, Mountain View, Calif.); the mature enzyme (residues 33-361) was expressed in *E. coli* cells using a pET 32a expression vector (Novagen, Darmstadt, Germany) with several modifications as described previously in Taiwan Patent Application No. 094132349. SeMet-labeled protein was produced in *E. coli* using a non-auxotrophic protocol and purified in a manner similar to the native protein. In addition, the mutants of human QC were constructed using a "QuickChange site-directed mutagenesis kit" (Stratagene, La Jolla, Calif.) and were expressed and purified in the same manner as the wild-type human QC.

Example 2

Crystallization of Human QC

Purified human QC was concentrated to 8-10 mg/ml and crystallized at 25° C. by the hanging drop vapor diffusion method. Rhombohedral crystals for wild-type, SeMet-labeled and mutant human QC were grown using equal volumes of the protein solution and the reservoir that contained 1.6-1.8 M $(NH_4)_2SO_4$, 4% dioxane and 100 mM MES, pH 6.5. In the condition of pH 8.0, the MES buffer in the reservoir was replaced by Tris-HCl.

In the case of substrate-bound form, the crystals of the mutant E201Q (grown at pH 7.0) were soaked for 1.5 hours into a solution consisting of 75% mother liquor, 25% glycerol and 1.1 M glutamine t-butyl ester. X-ray diffraction experiments were performed at various synchrotron beamlines as listed in Table 1. Prior to mounting on the X-ray machine, crystals were briefly soaked in mother liquor containing 20-25% glycerol (v/v) as cryoprotectants. All diffraction data were processed and scaled using the HKL package (Otwinowski et al., *Methods Enzymol.* 276: 307-326 (1997)). The space group of these crystals is R32, with typical unit cells of a=b=119 Å, c=333 Å, in which an asymmetric unit comprises two human QC molecules.

TABLE 1

| MAD phasing statistics | | | |
|---|---|---|---|
| Data set* | SeMet-QC λ1 | SeMet-QC λ2 | SeMet-QC λ3 |
| Wavelength (Å) | 0.9792 | 0.9794 | 0.9750 |
| Space group | | R32 | |
| Resolution (Å) | | 50-1.8 | |
| | | (1.86-1.80)† | |
| Total observations | 497057 | 497051 | 497136 |
| Unique reflections | 84184 | 84209 | 84238 |
| Redundancy | | 5.9 (5.6) | |
| Completeness (%) | | 100.0 (100.0) | |
| I/σ(I) | 21.1 (4.7) | 25.2 (4.9) | 27.4 (4.9) |
| $R_{merge}$ (%) | 7.8 (36.0) | 6.4 (34.1) | 6.2 (33.2) |
| Figure of merit and Z-score (SOLVE)0.65, 112.2 | | | |
| (at resolution range of 15-2.0 Å) | | | |

*X-ray diffraction experiment was performed at the beamline 5, KEK Photon Factory (Tsukuba, Japan).
†Values in parentheses correspond to highest resolution shell.

Example 3

Structure Determination and Refinement of Crystal of Human QC

The human QC structure at pH 6.5 was solved by the Multiwavelength anomalous diffraction (MAD) phasing method using the program SOLVE (Terwilliger et al., *Methods Enzymol.* 374: 22-37 (2003)). Having the MAD data at 20 to 2.0 Å resolution range collected at the wavelengths of 0.9792 Å (peak), 0.9794 Å (edge) and 0.9750 Å (high-energy remote) (see Table 1), all 14 Se atom sites were successfully located in the asymmetric unit. Subsequently, the program RESOLVE (Terwilliger et al., *Methods Enzymol.* 374: 22-37 (2003)) was performed where the initial electron density was modified by solvent flattening, and up to 83% of the protein model was automatically built using the entire MAD data of 50 to 1.8 Å resolution. Manual building of the remaining model and further refinement were carried out using the program O (Jones et al., *Acta Crystallogr. A* 47: 110-119 (1991)) against a 1.66 Å resolution data set of the wild-type crystal. The isomorphous structures of the mutants, different pH values and the substrate-bound and inhibitor-bound forms were phased using the refined model. For each structure, iterative cycles of model building with the program 0 and computational refinement with crystallography NMR system (CNS) (Brunger et al., *Acta Crystallogr. D* 54: 905-921 (1998)) were performed. $R_{free}$ values were calculated using 5% reflections. The stereochemical quality of the refined structures was checked using the program PROCHECK (Laskowski et al., *J. Appl. Crystallogr.* 26: 283-291 (1993)). Each of the final refined structures included 323 out of the 329 total residues in a human QC molecule, with a small disordered region of residues 183 to 188. Well-ordered water molecules were located and included in the models. The molecular figures were produced using the programs such as MOLSCRIPT (Kraulis et al., *J. appl. crystallogr.* 24: 946-950 (1991)), Raster3D (Merrit & Bacon et al., *Methods Enzymol.* 277: 505-524 (1997)) and GRASP (Nicholls et al., *Proteins* 11: 281-296 (1991)).

Example 4

Structure of the Active Site of Human QC

The active site is mainly created by six loops between α3-α4, β3-α5, β4-7, β5-α8, α8-α9 and β6-α10 (FIG. 2). The catalytic pocket is near the C-terminal edge of the central parallel strands β3, β4 and β35 (FIG. 1). It is relatively narrow but accessible to the bulk solvent via a solvent channel. The single zinc ion of human QC lies at the bottom of the active-site pocket and is tetrahedrally coordinated to O delta (δ) 2 of Aspartic acid residue (D) 159 (D159 Oδ2), O epsilon (ε) 1 of Glutamic acid (E) 202 (E202 Oε1), N epsilon (ε) 2 of Histidine (H) 330 (H330 Nε2), and a water molecule. In addition, several other completely conserved residues, including E201, W207, D248, D305, F325, and W329, abut the zinc environment (see FIG. 3), suggesting some roles in catalysis. Mutations of those amino acids decreased enzyme activity significantly as evident in Table 2. The acidic residues E201, D248 and D305 are pointing to each other at both pH 6.5 and 8.0, likely forming hydrogen bonds between them. The peptide bond between the zinc-coordinated D159 and the following S160 adopts a cis-configuration, stabilized by a network of hydrogen bonds, including D159 Oδ1-H140 Nε2 (2.70 Å), S160 Oγ-D248 Oδ1 (2.66 Å), D159 O-water (2.65 Å), and S160 N-water (2.80 Å).

TABLE 2

Kinetic parameters of wild-type and mutant human QC

|  |  | $K_m$ (mM) | $k_{cat}$ (s$^{-1}$) | $k_{cat}/K_m$ (mM$^{-1}$s$^{-1}$) |
|---|---|---|---|---|
| Wild | pH 7.0 | 0.79 ± 0.13* | 7.30 ± 0.01 | 9.459 ± 1.544 |
|  | pH 7.5 | 0.90 ± 0.09 | 9.76 ± 1.47 | 11.104 ± 2.716 |
|  | pH 8.0 | 0.63 ± 0.01 | 8.63 ± 0.48 | 13.663 ± 0.497 |
|  | pH 8.5 | 0.90 ± 0.05 | 9.93 ± 0.30 | 11.044 ± 0.331 |
|  | pH 8.8 | 2.06 ± 0.62 | 8.56 ± 1.55 | 4.319 ± 0.544 |
| Mutant† | R54W | 0.76 ± 0.04 | 7.35 ± 0.26 | 9.704 ± 0.824 |
|  | K144A | 1.47 ± 0.02 | 11.67 ± 0.34 | 7.944 ± 0.368 |
|  | F146A | 0.82 ± 0.16 | 7.91 ± 2.14 | 9.536 ± 0.769 |
|  | E201D | 12.62 ± 2.98 | 0.87 ± 0.28 | 0.068 ± 0.007 |
|  | E201Q‡ |  |  | ND |
|  | W207L | 1.77 ± 0.07 | 0.43 ± 0.01 | 0.243 ± 0.002 |
|  | W207F | 0.59 ± 0.05 | 2.32 ± 0.07 | 3.943 ± 0.189 |
|  | D248A‡ |  |  | ND |
|  | Q304L | 1.16 ± 0.09 | 9.39 ± 1.18 | 8.028 ± 0.386 |
|  | D305L‡ |  |  | ND |
|  | F325A | 4.67 ± 0.24 | 12.91 ± 0.06 | 2.772 ± 0.132 |
|  | W329A | 29.53 ± 2.29 | 1.35 ± 0.07 | 0.046 ± 0.001 |

*Values are represented as mean ± S.D. (n = 2 or 3).
†The assays for mutants were carried out under pH 8.0.
‡E201Q, D248A and D305L were shown to possess the ≈0.001%, ≈0.1% and ≈0.03% activity of the wild-type enzyme, respectively.
ND: Not detectable.

Figure 3:
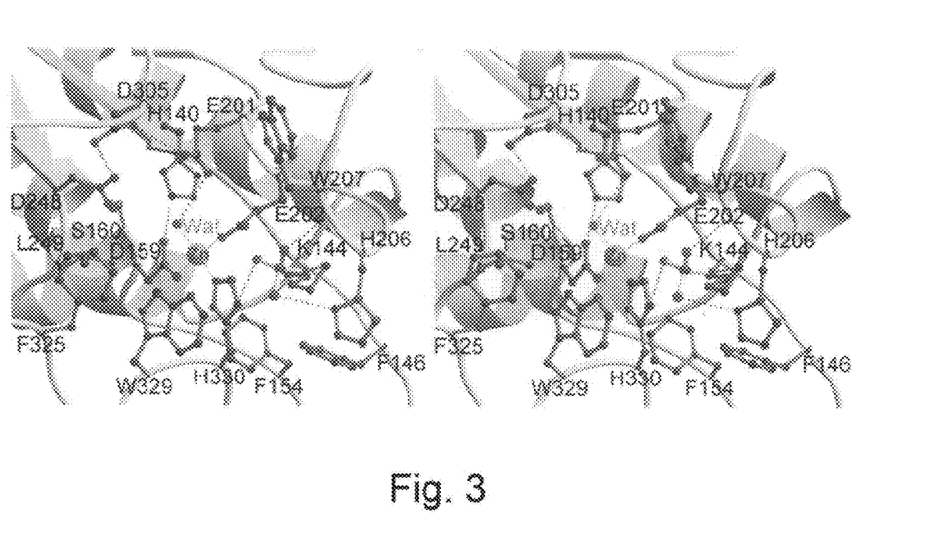
FIG. 3 is a stereo view of the human QC catalytic region.

The hydrophobic active-site pocket is lined by residues K144, F146, F154, L249, I303, I321, F325, and W329, having approximate dimensions of 13×11×7 Å$^3$. There are six water molecules located inside the pocket, including the water coordinated to the zinc ion. In addition, a sulfate ion is located near the opening of the pocket, hydrogen-bonded to K144 Nζ, H206 Nδ1, W207 N, H330 Nδ1, and several water molecules (FIG. 3). The active-site residues are shown and labeled. Possible hydrogen and coordination bonds are represented with dotted lines colored cyan and yellow, respectively. The green dotted lines depict the possibly unusual hydrogen bonds between D305 and E201 and between D305 and D248 of SEQ ID NO: 1

Example 5

The Structure of Enzyme-Inhibitor Complexes

In the preparation of the inhibitor-bound crystal forms, a 1.5 μl protein solution containing human QC was mixed with 0.5 μl inhibitor solution (100 mM) in a 2 μl reservoir. The crystals formed as a result were subjected to X-ray diffraction and process as described in example 2. The crystal forms were determined and refined as described in example 3. As shown in FIGS. 5 through 7, binding of the inhibitors results in the removal of six water molecules within the active-site pocket, including the zinc-coordinated one which is replaced by an imidazole nitrogen of the inhibitors. The inhibitors adopt different orientations, due to their different modifications on the imidazole ring. The small vinyl moiety of 1-vinylimidazole shows no interaction with the active site of human QC, leaving a large space in the catalytic pocket after its binding (FIG. 5). However the bulky hydrophobic phenyl ring on 1-benzylimidazole is closely surrounded and stabilized by the phenyl and indole groups of F325 and W329, respectively (FIG. 6). In contrast, the substituent of N-ω-acetylhistamine is oriented almost parallel to the backbone of segment G301-Q304, stabilized mainly by three additional hydrogen bonds to D248 Oδ2, Q304 N and Q304 O of the enzyme (FIG. 7). The detailed three-dimensional structures of human QC/1-vinylimidazole complex, human QC/1-benzylimidazole complex and human QC/N-ω-acetylhistamine complex are characterized by the atomic structure coordinates deposited as PDB ID codes 2AFZ, 2AFX and 2AFW, respectively in the protein data bank on the World Wide Web at pdb.org.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of identifying an inhibitor of a glutaminyl cyclase, comprising:
   (a) obtaining a three-dimensional representation of a human glutaminyl cyclase protein defined by the atomic coordinates of a crystal, wherein the crystal comprises a protein that consists of amino acid residues 33-361 of SEQ ID NO:1, and the crystal is characterized by a space group of R32 or H32 and has unit cell dimensions of a=b=119 Å, c=333 Å;
   (b) employing the three-dimensional representation to design or select a potential inhibitor of the protein;
   (c) synthesizing the potential inhibitor; and
   (d) contacting the potential inhibitor with the glutaminyl cyclase to determine the ability of the potential inhibitor to inhibit the glutaminyl cyclase.

2. The method of claim 1, wherein the three-dimensional representation comprises the atomic coordinates of the human glutaminyl cyclase crystal at pH 6.5.

3. The method of claim 1, wherein the three-dimensional representation comprises an active site comprising amino acid residues 159, 202 and 330 of SEQ ID NO:1.

4. The method of claim 3, wherein the active site further comprises amino acid residues 201, 207, 248, 305, 325 and 329 of SEQ ID NO:1.

5. The method of claim 3, wherein the active site further comprises amino acid residues 144, 146, 154, 249, 303, 321, 325 and 329 of SEQ ID NO:1.

6. A method of identifying an inhibitor of a glutaminyl cyclase, comprising:
   (a) obtaining a three-dimensional representation of a human glutaminyl cyclase protein defined by the atomic coordinates of a crystal, wherein the crystal comprises a protein that consists of amino acid residues 33-361 of SEQ ID NO:1, and the crystal is characterized by a space group of R32 or H32 and has unit cell dimensions of a=b=118.99 Å, c=332.26 Å;
   (b) employing the three-dimensional representation to design or select a potential inhibitor of the protein;
   (c) synthesizing the potential inhibitor; and
   (d) contacting the potential inhibitor with the glutaminyl cyclase to determine the ability of the potential inhibitor to inhibit the glutaminyl cyclase.

7. The method of claim 6, wherein the three-dimensional representation has the atomic coordinates of the human glutaminyl cyclase crystal at pH 8.0.

8. The method of claim 6, wherein the three-dimensional representation comprises an active site comprising amino acid residues 159, 202 and 330 of SEQ ID NO:1.

9. The method of claim 8, wherein the active site further comprises amino acid residues 201, 207, 248, 305, 325 and 329 of SEQ ID NO:1.

10. The method of claim 8, wherein the active site further comprises amino acid residues 144, 146, 154, 249, 303, 321, 325 and 329 of SEQ ID NO:1.

* * * * *

SEQUENCE LISTING

<160> NUMBER OF SEQ ID NOS: 1

<210> SEQ ID NO 1
<211> LENGTH: 361
<212> TYPE: PRT
<213> ORGANISM: Homo sapiens

<400> SEQUENCE: 1

```
Met Ala Gly Gly Arg His Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
            115                 120                 125

Pro Thr Ala Lys Arg His Leu Val Leu Ala Cys His Tyr Asp Ser Lys
130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
            180                 185                 190

Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln
            260                 265                 270

Ala Ile Glu His Glu Leu His Glu Leu Gly Leu Leu Lys Asp His Ser
            275                 280                 285

Leu Glu Gly Arg Tyr Phe Gln Asn Tyr Ser Tyr Gly Gly Val Ile Gln
290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335
```

-continued

```
Glu Asn Leu Asp Glu Ser Thr Ile Asp Asn Leu Asn Lys Ile Leu Gln
            340                 345                 350

Val Phe Val Leu Glu Tyr Leu His Leu
            355                 360
```